US008492178B2

(12) United States Patent  
Carlson et al.

(10) Patent No.: US 8,492,178 B2  
(45) Date of Patent: Jul. 23, 2013

(54) METHOD OF MONITORING FABRICATION PROCESSING INCLUDING EDGE BEAD REMOVAL PROCESSING

(75) Inventors: Alan Carlson, Westborough, MA (US); Ajay Pai, Crystal, MN (US); Tuan D. Le, Porto Alegre (BR); Antony Ravi Philip, Apple Valley, MN (US)

(73) Assignee: Rudolph Technologies, Inc., Flanders, NJ (US)

( * ) Notice: Subject to any disclaimer, the term of this patent is extended or adjusted under 35 U.S.C. 154(b) by 551 days.

(21) Appl. No.: 12/527,981

(22) PCT Filed: Feb. 25, 2008

(86) PCT No.: PCT/US2008/054913
§ 371 (c)(1),
(2), (4) Date: Jul. 23, 2010

(87) PCT Pub. No.: WO2008/103994
PCT Pub. Date: Aug. 28, 2008

(65) Prior Publication Data
US 2011/0054659 A1 Mar. 3, 2011

Related U.S. Application Data

(60) Provisional application No. 60/891,289, filed on Feb. 23, 2007.

(51) Int. Cl.
*H01L 21/00* (2006.01)
(52) U.S. Cl.
USPC ................................ 438/22; 438/16; 438/725
(58) Field of Classification Search
USPC ............................................ 438/16, 725, 20
See application file for complete search history.

(56) References Cited

U.S. PATENT DOCUMENTS

| 4,764,969 | A | 8/1988 | Ohtombe et al. |
| 6,947,588 | B2 * | 9/2005 | Sim ............................... 382/149 |
| 7,197,178 | B2 | 3/2007 | Simpkins |
| 2006/0072807 | A1 * | 4/2006 | Bultman et al. ............... 382/149 |
| 2006/0199287 | A1 * | 9/2006 | Fu et al. ........................... 438/16 |
| 2007/0253616 | A1 | 11/2007 | Suto |

FOREIGN PATENT DOCUMENTS

| DE | 69800756 T2 | 8/2001 |
| DE | 10131665 A1 | 1/2003 |
| EP | 1607738 A1 | 12/2005 |
| JP | 2000049203 | 2/2000 |
| JP | 2001101414 A | 4/2001 |

OTHER PUBLICATIONS

PCT Search Report, Jun. 20, 2008, 10 pages.
English translation of the Notice of Rejection (JP2009-551059) dated Jan. 15, 2013 (1 page).

* cited by examiner

*Primary Examiner* — Phuc Dang
(74) *Attorney, Agent, or Firm* — Dicke, Billig & Czaja, PLLC

(57) ABSTRACT

Systems and method for monitoring semiconductor wafer fabrication processing, for example based upon EBR line inspection, including capturing at least one image of a wafer at an intermediate stage of fabrication. The captured image(s) are compressed to generate a composite representation of at least an edge zone of the wafer. An edge bead removal area is identified in the representation, and at least one feature attribute is extracted from the identified area. The extracted feature attribute is automatically assessed, and information relating to a status of the fabrication processing in generated based upon the assessment. For example, recommended modifications to the fabrication processing, either upstream or downstream of the current stage of fabrication (or both) can be generated and implemented.

17 Claims, 10 Drawing Sheets

METHOD OF MONITORING FABRICATION PROCESSING INCLUDING EDGE BEAD REMOVAL PROCESSING

CROSS-REFERENCE TO RELATED APPLICATION

This application is U.S. national stage application claiming priority under 35 U.S.C. §371 to International Application Serial No. PCT/US08/54913, filed Feb. 25, 2008, which claims the benefit of U.S. Provisional Patent Application Ser. No. 60/891,289 filed on Feb. 23, 2007; the teachings of all of which are incorporated herein by reference.

BACKGROUND

The present disclosure relates generally to systems and method for monitoring semiconductor wafer fabrication, for example by inspection of an edge exclusion zone of a wafer, including optimization fabrication process steps.

Over the past several decades, semiconductor-driven technologies have grown exponentially and have revolutionized our society. Manufacturers of semiconductors have made vast improvements in production, resulting in improved end product quality, speed, and performance. However, there continues to be demand for faster, more reliable, and higher performing semiconductors. To assist with these demands, better monitoring and/or inspection systems and methods are continuously being sought.

For reference, semiconductors are often manufactured in wafer format, with each wafer including a series of layers, including, for example, a silicon and insulator layer or layers in a silicon-on-insulator or SOI wafer. Regardless, during wafer production, masking layers or resist layers are often times applied to a wafer in order to facilitate wafer patterning. Typically, a desired amount of liquid resist is applied to a top surface of a wafer while the wafer is being rotated. As the wafer is rotated, the resist material spreads outward radially from the center of the wafer and toward the semiconductor edge such that the wafer is substantially coated with a circular layer of resist. Excess amounts of resist can accumulate and form a mound or bead of resist toward an outer edge of the semiconductor wafer. At times, the resist also flows over the wafer edge, which can contaminate an edge normal and a backside of the wafer. Various edge bead removal (EBR) processes are applied in order to eliminate the "edge bead" of resist and/or other unwanted material proximate the wafer edge.

It is also noted that during wafer production, various material removal processes are employed, including, for example, wet etches, a dry etches, polishing, chemical mechanical polishing (CMP), and others depending on the materials being removed. During EBR removal, for example, chemical EBR units remove a ring of resist and other unwanted material about the edge of the wafer by dispensing a solvent referred to as EBR fluid, onto the resist of the semiconductor wafer. The solvent dissolves or develops away the resist and allows for easy removal of the resist from the edge of the semiconductor wafer. Wafer edge exposure (WEE) units can be additionally or alternatively applied for EBR purposes. WEE utilizes an optical unit to expose a ring of resist at or near the edge of the semiconductor wafer to light. During subsequent development processes, the exposed ring of resist is removed.

Accurate placement of the edge exclusion region is critical to maintaining edge die yield. Variation in film overlay in the edge exclusion region can lead to yield-limiting defects. Edge Bead Removal (EBR) metrology or Edge Exclusion Width (EEW) metrology describes a topside surface measurement of the wafer edge exclusion region relative to the wafer center and the wafer edge. This measurement is typically made at several points along the wafer's edge and often ranges between 0 mm and 6 mm in width. In photolithography, EBR metrology data can be used to determine the repeatability of wafer alignment and the accuracy of EBR dispensing nozzles on the coat track.

In addition to EBR/EEW metrology, wafer edge inspection provides an indirect method to control the EBR process by detecting jaggedness of the EBR profile, scalloping, splashing, and other EBR line defects. Improper EBR can also create residuals on other edge surfaces that can lead to cross-contamination of wafers and handling equipment.

The EBR process is used directly after resist coating to remove excess photo resist around the perimeter of the wafer at a fixed distance from the wafer edge. The edge exclusion region can be created in two ways. In a chemical EBR process, a solvent is dispensed in this area as the wafer rotates to create an edge exclusion region. An optical EBR is created during wafer exposure by also exposing the photo resist around the perimeter of the wafer.

The EBR process is often overlooked as a mechanism that can cause front side damage. This is because EBR metrology (the ability to determine if the EBR is too big, too small, off-center, etc.) is still a manually intensive step in modern fabs. The most common method to measure EBR dimensions is to place the wafer onto an optical microscope and measure the distance from the EBR line to the wafer edge at three or more positions around the wafer.

This manual-type EBR measurement approach is oftentimes performed using a manual profiler that is also used to measure trench depths. The tool works by dragging a stylus across the wafer from the center outward. To measure EBR, the distance (measurement #1) is recorded from some reference point to the point where the stylus drops down from the resist height to the bare wafer where the EBR begins. The distance from the same reference point to the point where the stylus falls off the edge of the wafer (measurement #2) is also recorded. EBR width is calculated by subtracting measurement #1 from measurement #2. These measurements are taken at 3 points around the wafer, 120 degrees apart, as reflected in FIG. 1.

EBR measurements taken on the profiler can be susceptible to error. The tool is very sensitive to vibration, which can often result in false readings. The stylus can also give inaccurate readings on non-uniform wafer topography, requiring additional measurements. This process is time consuming, as it can take up to 10 minutes to measure 2 wafers using this method.

This manual approach can also be problematic for several other reasons. First, the wafer bevel transition can easily be mistaken for the wafer edge apex, leading to a smaller Edge Exclusion Width (EEW) measurement, thus compromising the integrity of the data. Secondly, the EBR line can be difficult to distinguish on patterned wafers, especially when some layers are patterned all the way to the edge. Additionally, the EBR line may be discontinuous around the wafer leading to erroneous measurement; and finally, three measurement points per wafer is insufficient to statistically represent the EBR characteristics of a wafer.

Manual EBR metrology is generally reserved for preventive maintenance using test wafers. As a result, infrequent sampling allows out-of-spec EBR to go unnoticed. Out of spec or off-center EBR can result in several different process-related issues. If the EBR width is too narrow, edge grippers on process tools can touch the hardened, brittle photoresist and cause it to crack and flake off, causing contamination. If the edge exclusion is too wide, there will be less surface area available for product die. The ITRS roadmap previously called for an edge exclusion of 2 mm. In 2007, this value changed to 1.5 mm to tie in with the 65 nm node.

Poor control of the Edge Bead Removal process leads to poor edge die yield. EBR control and accuracy are important with multiple stacked layers. If EBR is off-center, undercutting of films can lead to popping at the edge. Additionally, there is a correlation between out-of-spec EBR metrology and edge film adhesion. For example, an off-centered EBR indicates that part of the wafer edge is under-cleaned. A larger-than-usual EBR may indicate an edge "overhang" problem in a film stack. Unwanted film geometry along the wafer edge can cause unexpected film stress and reduce film adhesion to the substrate, resulting in delamination and flaking These defects can then be transferred to the front side of the wafer. This is particularly crucial in metal CMP where the delaminated metal flakes can move from the wafer edge and lodge between the polishing pad and the front surface of the wafer, causing severe front side scratches during the polishing step. If an EBR excursion is not detected in a timely manner, product may need to be reworked or scrapped.

In light of the above, a need exists for semiconductor fabrication monitoring systems and methods that rapidly and accurately characterize EBR-related feature(s), and implement, where necessary, alterations to the fabrication processing steps.

SUMMARY

Some aspects in accordance with principles of the present disclosure relate to systems and method for monitoring semiconductor wafer fabrication processing, for example based upon EBR line inspection. In some embodiments, the method of monitoring includes capturing at least one image of a wafer at an intermediate stage of fabrication. The captured image(s) are compressed to generate a composite representation (e.g., a composite image) of at least an edge zone of the wafer. An edge bead removal area is identified in the representation, and at least one feature attribute is extracted from the identified area. The extracted feature attribute is automatically assessed, and information relating to a status of the fabrication processing in generated based upon the assessment. For example, the status information can include a pass/fail designation for the wafer, as well as recommended modifications to the fabrication processing, either upstream or downstream of the current stage of fabrication (or both). The recommended modifications are automatically implemented in some embodiments. With this methodology, various feature attributes (e.g., EBR line widths, locations, centricity, etc.) can be quickly reviewed and process modifications implemented based on various factors, including historical component yield information.

DETAILED DESCRIPTION

Figure 1:
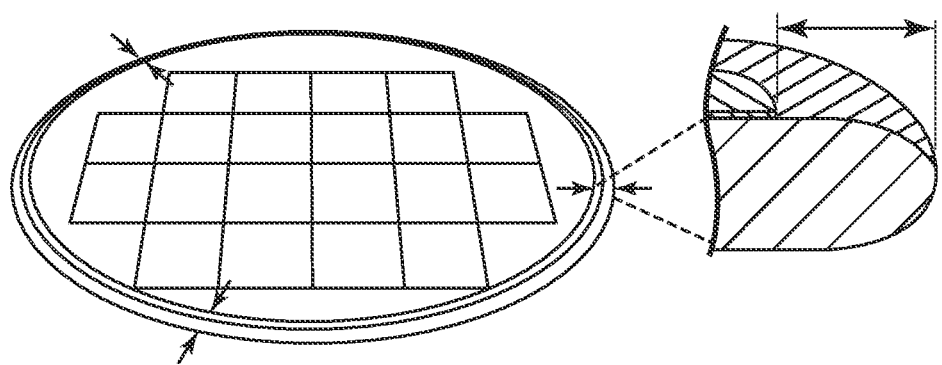
FIG. 1 is a simplified illustration of a prior art manual EBR metrology method.

In the following detailed description, reference is made to the accompanying drawings that form a part hereof, and in which is shown, by way of illustration, specific embodiments in which aspects of the present disclosure may be practiced. In the drawings, like numerals describe substantially similar components throughout the several views. These embodiments are described in sufficient detail to enable those skilled in the art to practice aspects of the present disclosure. Other embodiments may be utilized and structural, logical, and electrical changes may be made without departing from the scope of the present disclosure. The following detailed description is, therefore, not to be taken in a limiting sense, and the scope of the present disclosure is defined only by the appended claims and equivalents thereof.

In general terms, the present disclosure provides various semiconductor fabrication processing monitoring systems and methods that facilitate at least one of quick detection of EBR-related defects, as well as characterizing the quality of the EBR process. In connection with these characterizations, the monitored information can be employed to reveal a relationship between EBR-related defects and the quality of the EBR process, and can be used to make necessary adjustments to one or more processing steps, including "upstream" or "downstream" of the fabrication processing step at which monitoring occurs, and as a basis for wafer rework decisions. With some embodiments, proper tuning and monitoring of the EBR/EEW process allows for the eventual elimination of an entire class of EBR-related defects, thus significantly increasing edge die yield.

In light of the above, aspects of the present disclosure provide monitoring systems and methods positioned or performed during an intermediate stage of the semiconductor wafer fabrication processing, for example following EBR.

More particularly, monitoring is performed to obtain and evaluate edge image data from top, normal, and/or bottom directions in order to identify or locate various wafer features, including, but not limited to, wafer features proximate the wafer edge (such as wafer notch locations; various film layer edge locations, such as resist edge locations, insulator and/or silicon layer edge locations, or other locations; layer thicknesses, such as resist thickness or silicon layer thicknesses; wafer edge locations; resist edge to wafer edge offsets; edge bevel geometries and locations; and others) as well as other wafer features (such as wafer centers; resist layer centers; and wafer center to resist center offsets; and others), using data collected from edge imaging. As a point of reference, "inspecting" a wafer is used in this disclosure as a subset of "monitoring" of the fabrication processing; thus, the systems and methods of monitoring in accordance with the present disclosure include inspecting a wafer along with one or more other operational steps.

The characteristics of wafer features, including those described above, are often affected by material application and/or removal processes employed during wafer production. Thus, in some embodiments, evaluation/inspection of such features, including feature location, metrology, and/or other characterization is used to control such processes, for quality control, and/or to improve yields, for example. Some embodiment wafer edge inspection systems and methods are useful for measuring the EBR line feature. For reference, an "EBR line" is indicative of a resist edge formed during an EBR process. Though the terms "resist edge," "edge of the resist," "edge bead removal lines," or "EBR lines" are generally used interchangeably herein, it should be understood that principles of the present disclosure apply to resist edges and other wafer features formed via a variety of wafer fabrication processes, inclusive of, but not limited to, edge bead removal (EBR) processes. Regardless, in some embodiments, wafer edge monitoring and/or inspection systems and methods help better ensure that wafer processing is proceedingly correctly. For example, some embodiments include measuring EBR line position relative to a center of a wafer and/or relative to an edge of the wafer to provide information relating to whether the wafer is being properly centered during EBR processes and/or resist deposition processes.

As a part of inspecting one or more wafer features, some embodiment monitoring systems and methods include acquiring a series of digital images about an edge portion of a wafer, for example with an associated sensor, such as an optical camera, positioned at a radial offset from a center of a rotating stage assembly. In some embodiments, an entire outer circumference of the wafer is imaged in a continuous and/or stepwise fashion. Edge images are compressed and evaluated cumulatively, for example via concatenation into a composite representation (e.g., image), in order to characterize various wafer features such as those described above. For example, the distance from the edge of the wafer to a resist edge, such as an EBR line, is optionally evaluated about an entire circumference of the wafer. Any number of resist layers can be present on the wafer, each resist layer defining a resist edge. Thus, where applicable, each of a plurality of resist edges of interest is located as desired.

Additionally, it is contemplated that information obtained by imaging the wafer edge, such as a computed wafer center location, wafer edge location, the locations of resist edges, and/or others can be used in related monitoring processes and systems. For example, wafer center location can be used for reporting and analyzing wafer defects. Wafer edge location is optionally used to help an inspection camera positioned to image a profile or side of the wafer edge ("normal edge") to track the normal edge and permit the camera to maintain proper focal distance from the normal edge of the wafer. Thus, in some embodiments, information collected with the monitoring systems and methods is used as part of a larger, more detailed wafer characterization system or monitoring methodology.

Figure 2:
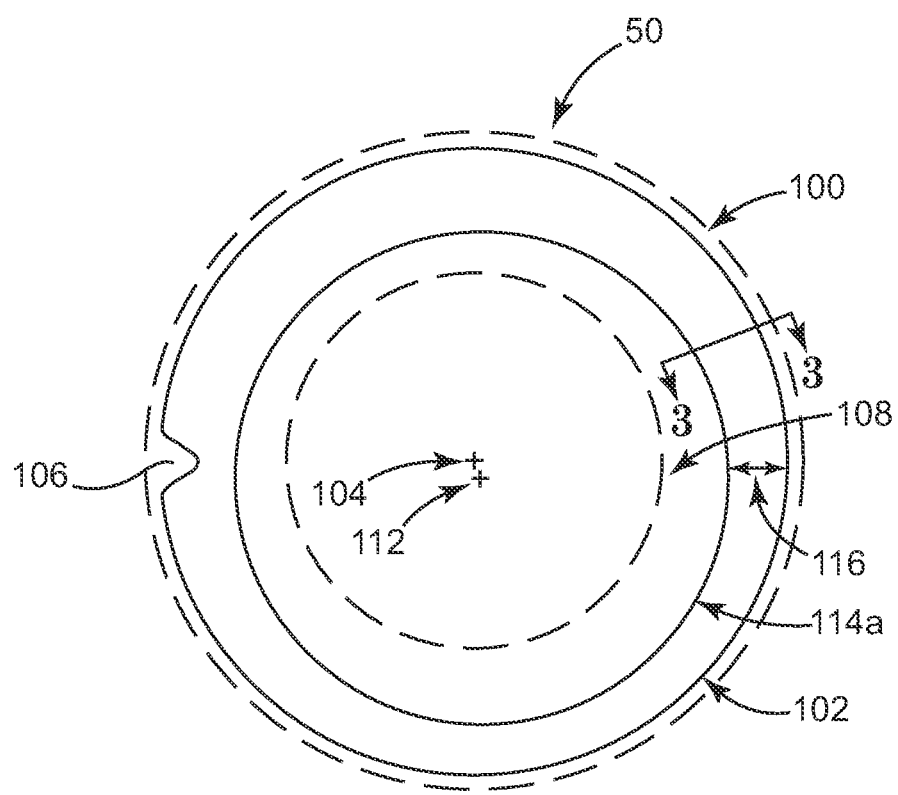
FIG. 2 is a schematic, top view of a semiconductor wafer at an intermediate stage of fabrication processing to be monitored in accordance with principles of the present disclosure.

With the above background in mind, FIG. 2 illustrates a top view of a semiconductor wafer 50 at an intermediate stage of fabrication processing. The wafer 50 defines a top edge region 100 extending annularly about the wafer 50. The wafer 50 also includes a wafer perimeter edge 102, a wafer center 104, a wafer notch 106, a layer of resist 108, a resist center 112, a first resist edge 114a, for example a first EBR line, a second resist edge 114b (FIG. 9B), for example a second EBR line, and a distance 116 between the wafer perimeter edge 102 and the first resist edge 114a. The top edge region 100 extends from a portion of the layer of resist 108 proximate the first resist edge 114a to beyond the wafer perimeter edge 102 about the circumference of the wafer 50. In some embodiments, both the wafer 50 and the layer of resist 108 are highly circular in shape.

FIG. 2 further illustrates the resist center 112 at offset from the wafer center 104. This type of inconsistency can arise due to operator or mechanical error during formation of the resist 108 and/or removal of portions the resist 108. As previously alluded to, a location of a center of rotation of wafer 50 during fabrication affects the location of resist 108 relative to the wafer center 104, which, in turn, varies the distance 116 between the wafer perimeter edge 102 and the resist edge 114a about the top edge region 100. For example, in some embodiments, during various automated fabrication steps the wafer 50 is secured on a chuck, or stage assembly. However, due to automation or other errors, a center of rotation of the wafer 50 can be misaligned from the wafer center 104. When the relative center of rotation is not aligned with the wafer center 104, resist or other layers are often eccentrically positioned relative to the wafer center 104 and the wafer perimeter edge 102.

FIG. 2 illustrates the resist center 112 at an exaggerated offset from the wafer center 104, such that the misalignment between the two centers 104, 112 as well as non-uniformity of the distance 116 between the wafer edge 102 and the first resist edge 114a is readily discernable. However, in practice, misalignment (i.e., deviation from a desired degree of alignment) between centers 104, 112 and edges 102, 114a is often difficult to observe with the naked human eye.

Figure 3A:
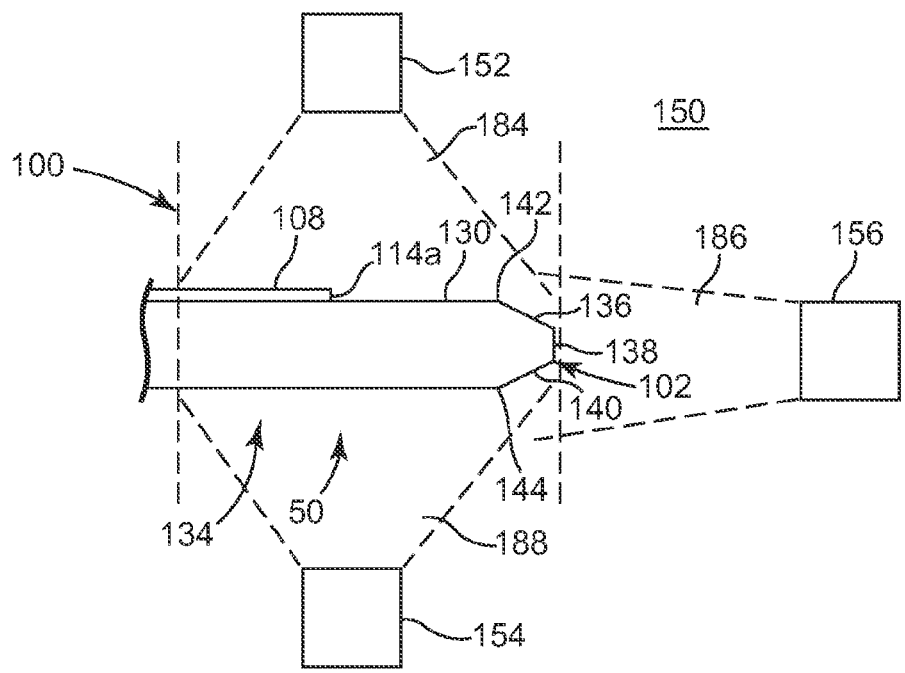
FIG. 3A is a schematic, sectional view of the wafer of FIG. 2 along line 3-3 and a portion of an associated fabrication monitoring system in accordance with principles of the present disclosure.

FIG. 3A provides a sectional view of the wafer 50 along line 3-3 as indicated in FIG. 2, along with components of a system in accordance with aspects of the present disclosure as described below. The top edge region 100 includes the wafer edge 102, the first resist edge 114a, and an exposed edge region 130 which is substantially free of the resist 108 and/or other unwanted surface materials. With reference between FIGS. 2 and 3A, in some embodiments, the top edge region 100 is substantially annular in shape defining an inner diameter substantially inset from various edge features of interest, such as inset from an edge of the exposed region 130 and/or the resist edge 114a. Also shown is a bottom edge region 134 opposite the top edge region 100 which can also be substantially free of resist or other film layers and is optionally a mirror image of the top edge region 100 being defined by about the same boundaries. In some embodiments, the wafer 50 is beveled proximate the wafer edge 102 and defines a top bevel 136, a wafer edge normal 138, and a bottom bevel 140. The top bevel 136 has an origin 142 and extends to the wafer edge normal 138. The wafer edge normal 138 can generally be described as an outer face and boundary of the wafer 50, thus defining a location of the wafer edge 102. In turn, the bottom bevel 140 defines an origin 144 and extends to the wafer edge normal 138.

Figure 4:
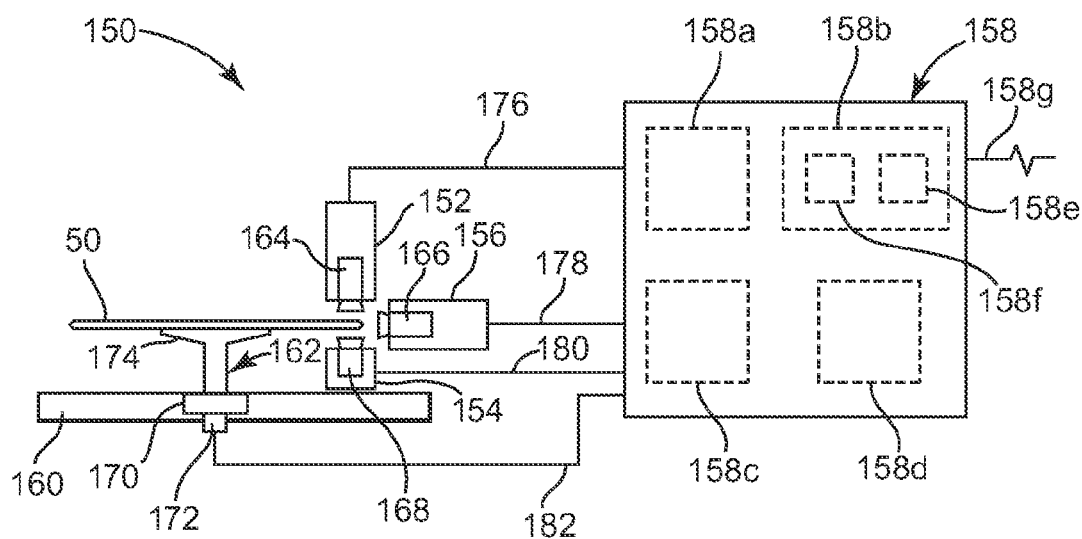
FIG. 4 is a schematic view illustrating the wafer of FIG. 2 and the monitoring system of FIG. 3A in more detail.
Figure 3B:
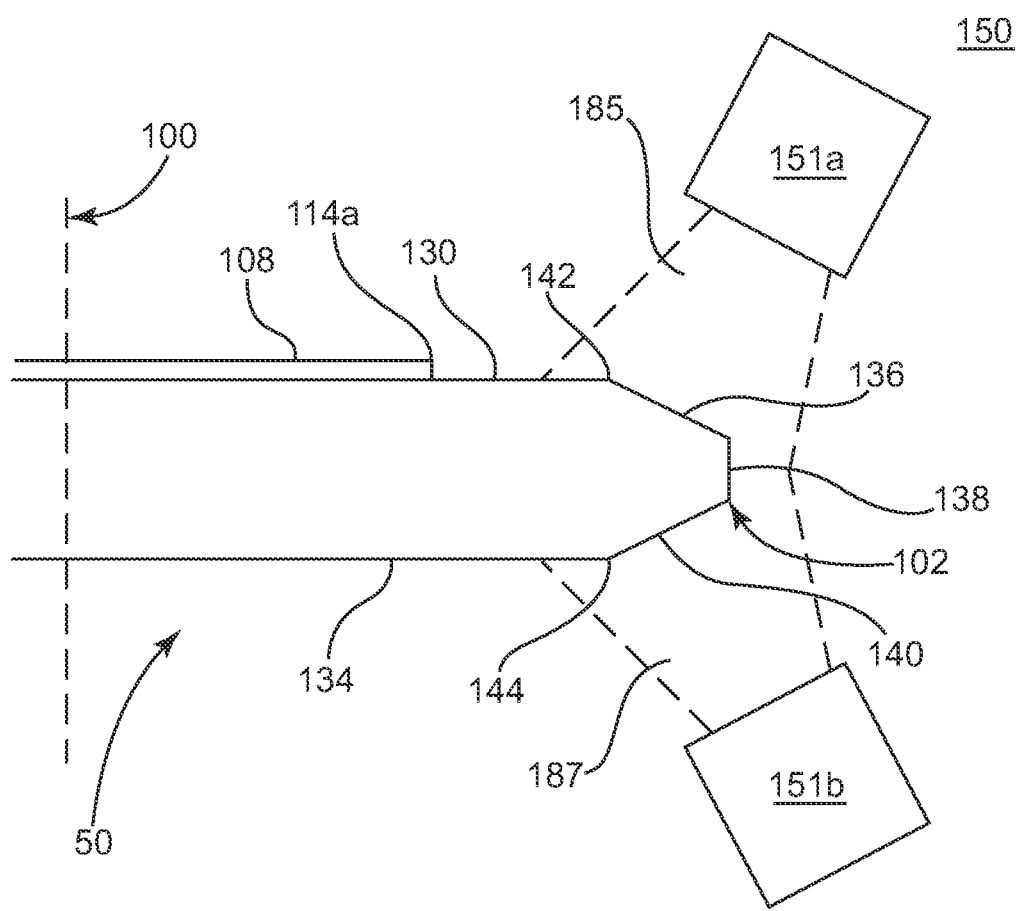
FIG. 3B is a schematic view of a portion of another monitoring system useful with or apart from the monitoring system of FIG. 3A.

FIG. 3A also illustrates a portion of a monitoring system 150 according to some embodiments of the present disclosure, with FIG. 4 showing a more inclusive schematic of the monitoring system 150. With reference between FIGS. 3A and 4, the monitoring system 150 includes, in some embodiments, a top edge sensor 152, a bottom edge sensor 154, an edge normal sensor 156, a controller 158, a base 160, and a stage assembly 162. Alternatively or additionally, and as shown in FIG. 3B, the system 150 can include a top bevel sensor 151a and a bottom bevel sensor 151b. The top and bottom bevel sensors 151a, 151b can be akin to the sensor 152-156, provided as two dimension imaging sensors, line scan imaging sensors, etc.

The controller 158 includes a computing or processing device programmed to operate various modules, such as program modules for operating the monitoring system 150. In some embodiments, the controller 158 includes an image acquisition module 158a for receiving image data from one or more of the edge sensors 152, 154, 156, a composite module 158b for generating a composite representation of compressed images, an image analysis module 158c for analyzing the composite image to identify one or more wafer features, and a user interface module 158d for optionally displaying the composite representation and/or other information to a user as described below. The composite image module 158b further includes an image concatenating module 158e for stitching the images and an image compression module 158f for compressing the images. In some embodiments, the controller 158 further includes one or more electronic links (wired or wireless) 158g to separate controller(s) otherwise operating or controlling operations of fabrication processing equipment (or a central fabrication server). As described below, the controller 158 is optionally programmed to effectuate determined process modifications by prompting of the separate controller(s) via the link(s) 158g. The system 150, including the various modules 158a to 158f of the controller 158, is adapted to perform edge inspection and evaluation of wafer features according to various embodiment methods of monitoring semiconductor fabrication processing edge described below.

The top edge sensor 152 includes a camera 164, the edge normal sensor 156 includes a camera 166, and the bottom edge sensor 154 includes a camera 168. The stage assembly 162 includes a motor 170, an encoder 172, and a support plate 174. The motor 170 is coupled to the encoder 172 and the support plate 174, such that the motor 170 is adapted to rotate the support plate 174. The encoder 172 provides counts for controlling the position of motor 170 (and thus the support plate 174), although other methods/apparatuses for controlling a position of the motor 170 are contemplated. The various sensors 152, 154, and/or 156 are generally adapted to capture images of the wafer 50, such as grayscale and/or color image data for example. Additionally, it should be understood that it is contemplated that the sensors 152, 154, 156 optionally operate according to a variety of principles or categories thereof, including for example, optical imaging, x-ray imaging, interferometric, Shack-Hartmann wavefront, and/or confocal principles in some embodiments.

The support plate 174 supports the wafer 50 during rotation and imaging of the wafer 50. The controller 158 is electrically coupled to the top edge sensor 152 through the communication link 176, to the edge normal sensor 156 through the communication link 178, to the bottom edge sensor 154 through the communication link 180, and to the stage assembly 162 through the communication link 182. The controller 158 controls the top edge sensor 152, the edge normal sensor 156, the bottom edge sensor 154, and the stage assembly 162 through the communication links 176, 178, 180, 182 for inspection of the top edge region 100, the bottom edge region 134, and/or the edge normal 138.

In particular, in some embodiments, the wafer 50 is inspected with the monitoring system 150 from top, normal, and/or bottom directions, with various angles of inspection contemplated. In general terms, the monitoring system 150 performs "top-down" inspection of the top edge region 100 (FIG. 3A) via the top edge sensor 152. The monitoring system 150 additionally or alternately performs "bottom-up" inspection of the bottom edge region 134 proximate via the bottom edge sensor 154 and/or the wafer edge normal 138 via the edge normal sensor 156. In some embodiments the monitoring system 150 inspects an edge portion of the wafer 50, the edge portion including one or more of the top edge region 130, the bottom edge region 134, and/or the wafer edge normal 138 by acquiring image data at a plurality of circumferential image frame locations about the wafer 50. For example, the first resist edge 114a, the exposed edge region 130, the top bevel 136, and the wafer edge 102 are all optionally imaged about the wafer 50 with the top edge sensor 152. In turn, the bottom edge sensor 154 and/or the edge normal sensor 156 are optionally used to image the bottom edge region 134 and edge normal 138, respectively about the entire wafer 50 or a portion thereof.

In particular, with reference to FIGS. 3A and 3B, the top edge sensor 152 has an inspection area 184, the edge normal sensor 156 has an inspection area 186, the edge bottom sensor 154 has an inspection area 188. The top bevel sensor 151a has an inspection area 185, and the bottom bevel sensor 151b has an inspection area 187. As can be seen in FIG. 3B, the inspection area 185 can encompass the bevel 136 of the wafer edge 102, as well as portions of the edge top 130 and the edge normal 138. Similarly, the inspection area 187 can encompass the bottom bevel 140, as well as portions of the edge normal 138 and the edge bottom 134. In some embodiments, the edge inspection system 150 inspects the top edge region 100 of the wafer 50 including the first resist edge 114a, the exposed edge region 130, and the top bevel 136; the edge normal 138; and the bottom edge region 134 including the bottom bevel 140, according to the inspection areas 184, 186, 188, respectively. It should be understood that, in some embodiments, the top edge region 100 generally corresponds to the inspection area 184. Brightfield illumination is used in some embodiments, although darkfield illumination, any of which may utilize monochromatic, selected wavelength, and/or broadband illumination, combinations of darkfield and brightfield illumination, and other imaging techniques such as those previously referenced are also contemplated.

The monitoring system 150 can assume a variety of forms differing from those described above. For example, the system 150 can incorporate less than five of the sensors 151a-156 (e.g., only the top edge sensor 152 and/or the edge normal sensor 156 are provided). Regardless, the controller 158 is further programmed to perform various steps in accordance with methods of the present disclosure describe below.

Figure 5:
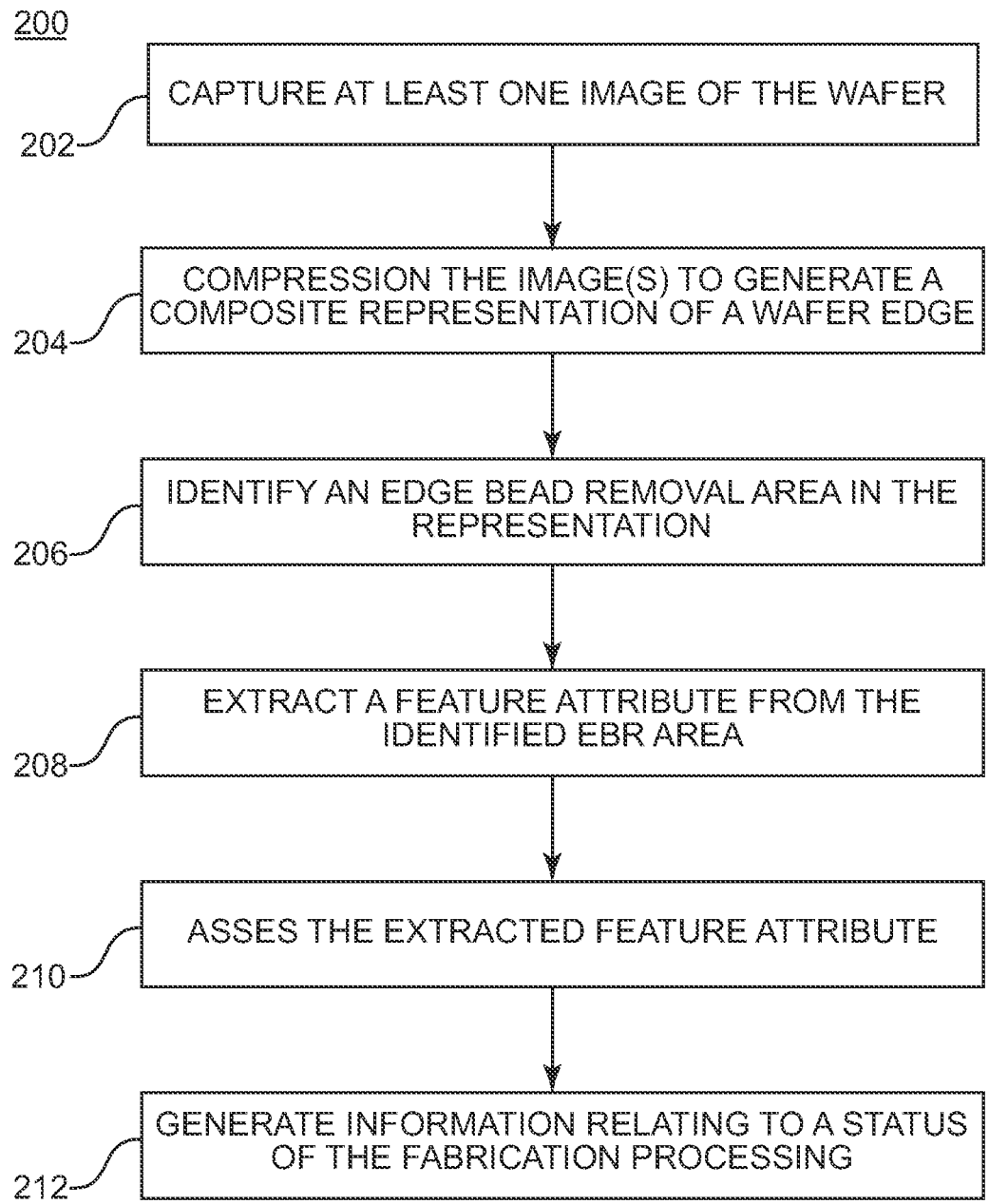
FIG. 5 is a flow diagram of methods of monitoring semiconductor fabrication processing in accordance with principles of the present disclosure.

More particularly, and with additional reference to the flow diagram of FIG. 5, a monitoring method 200 in accordance with aspects of the present disclosure includes capturing at least one image of the wafer 50 as described below at 202. As a point of reference, the monitoring method 200 is performed, in some embodiments, on the wafer 50 at an intermediate stage of the semiconductor fabrication processing, for example immediately following EBR step(s). Further, the captured image(s) can be generated by one of the sensors 151a, 151b, 152, 154 and/or 156, and in some embodiments a plurality of images of the wafer 50 are captured via one, two or all of the sensors 151a-156.

Regardless of the number of captured images, at 204, image compression is performed to generate a composite representation (e.g., a composite image) of an edge zone of the wafer 50. Several acceptable image compression techniques are described in greater below. In general terms, and in some embodiments, the image compression converts various features of the wafer 50 along the edge zone (e.g., EBR lines, wafer perimeter edge, wafer notch, etc.) into a singular, two-dimensional representation of all the feature(s). For example, a circular ring feature can be converted to a straight line; an oblong feature can be converted to a curvilinear or curved (e.g., sinusoidal) line; etc.

The representation of the edge zone is reviewed and an edge bead removal area identified at 206. The identified edge bead removal area is generally inclusive of the wafer perimeter edge as represented in the composite representation, as well as any EBR lines represented (or expected EBR line(s) as described below) in the composite representation. Thus, for example, in some embodiments, the identification at 206 entails identifying a representation of the top edge 100 in the composite representation. Alternatively, the identified edge bead removal area can be a pre-determined feature of interest that is identifiable in the composite representation (e.g., an EBR line, a wafer perimeter edge, etc.).

At least one feature attribute is extracted from the identified edge bead removal area at 208. The feature attribute, as well as the methodology by which it is extracted from the composite representation, can assume a variety of forms. In some embodiments, the feature is an EBR line discernible in the composite representation. Under these circumstances, the feature attribute can be or relate to a width of the EBR line. For example, the extracted EBR line width attribute can be a maximum width, a minimum width, an average width, a mean width, a standard deviation in width, etc., along the EBR line as characterized in the composite representation. In this regard, where the feature attribute to be extracted at 208 relates to a mathematical function of the EBR line feature (e.g., standard deviation of EBR line width), the EBR line width can be designated as a feature characteristic (e.g., the feature attribute is a function of the feature characteristic), with the method of extracting including determining a value of the feature characteristic at a plurality of points along the EBR line as characterized in the composite representation. The extracted feature attribute is then determined by applying a mathematical function to the determined values. For example, where the feature attribute is standard deviation in EBR line width, extracting the feature attribute can include determining a width of the EBR line (as reflected in the composite representation) at a plurality of points (e.g., more than 5 points, alternatively more than 50 points) and then calculating the standard deviation of the so-determined values.

Alternatively or additionally, the feature attribute can be or relate to a distance between the EBR line and an outer perimeter of the wafer as characterized in the composite representation. For example, the extracted EBR line-outer perimeter distance attribute can be a maximum distance, a minimum distance, an average distance, a mean distance, a standard deviation in distance, etc., as characterized in the composite representation. In this regard, where the feature attribute to be extracted at 208 relates to a mathematical function of the EBR line-outer perimeter distance feature (e.g., standard deviation of EBR line-outer perimeter distance), the distance can be designated as a feature characteristic (e.g., the feature attribute is a function of the feature characteristic), with the method of extracting including determining a value of the feature characteristic at a plurality of points along the EBR line as characterized in the composite representation. The extracted feature attribute is then determined by applying a mathematical function to the determined values. For example, where the feature attribute is mean distance between the EBR line and the outer perimeter of the wafer, extracting the feature attribute can include determining a distance between the EBR line and the outer perimeter (as reflected in the composite representation) at a plurality of points (e.g., more than 5 points, alternatively more than 50 points) and then calculating the mean distance of the so-determined values.

Alternatively or additionally, the extracted feature attribute can be a relationship between two (or more) features in the composite representation. For example, the features can be adjacent EBR lines, and the extracted feature attribute indicative of a likelihood that the EBR lines overlap one another. More particularly, in some embodiments, the extracted feature attribute includes a characterization of whether or not the EBR line features cross over one another in the composite representation. Alternatively, the extracted feature attribute includes a characterization of a comparison of a determined standard deviation in mean positioning of a first EBR line with a determined standard deviation in mean positioning of a second EBR line, based upon the representations of the first and second EBR lines in the composite representation.

Alternatively or additionally, the extracted feature attribute can be an extent of completeness of a feature, such as an extent of completeness of an EBR line feature. As a point of reference, an entirety of a properly formed EBR line will be within, and spaced internally from, an outer perimeter of the wafer 50. Thus, a properly formed EBR line will define a continuous ring (noting that the ring may or may not be a perfect or near-perfect circle; any deviations from a true circle can serve as alternative extracted feature attributes). Where, however, the EBR processing is deficient, the EBR line, or segment(s) thereof, can extend to the wafer outer perimeter, with the segment(s) "at" the wafer outer perimeter effectively being obliterated (i.e., a discernible EBR line does not exist at the wafer outer perimeter). The extent of completeness attribute thus represents a deviation of an identified EBR line feature from a complete ring (or other continuous shape) and can be expressed, for example, as a percentage of the EBR line found in the composite representation as compared to a "complete" EBR line. By way of example, then, it would be expected that an EBR line feature reflected in a composite representation will have a "length" commensurate with a length of the wafer outer perimeter (as reflected in the composite representation); where an actual EBR line feature in the composite image has a length that is 75% of the wafer outer perimeter length, the extracted feature attribute can be characterized as a 75% extent of completeness. In other words, with this one example, the extracted feature attribute characterizes the EBR line feature as being 75% complete.

Alternatively or additionally, the extracted feature attribute can be centricity of a feature, such as centricity of an EBR line feature. More particularly, centricity of a feature relative to an identified center of the wafer (as reflected in the composite representation) can be determined (e.g., percent of centricity relative to a 100% concentric baseline) and established as the extracted feature attribute. As a point of reference, the EBR line can be non-centric relative to the wafer center due to various processing variables, such as resist or film deposition, EBR processing off-set, etc. One or more different variables can contribute to centricity deviations of other features of interest.

Alternatively or additionally, the extracted feature attribute can be or relate to absence of an expected feature, such as absence of an expected EBR line feature. For example, the predetermined layout and "recipe" of a particular semiconductor wafer (or series of wafers) will prescribe the location(s) of EBR line(s) along the wafer and relative to the wafer outer perimeter. Even if the wafer being inspected as part of the monitoring process is not perfectly formed, EBR line(s) will be reflected in the composite representation at or along a location relative to the wafer outer perimeter approximating or commensurate with the predetermined or expected location (it being understood that the wafer outer perimeter is identifiable in the composite representation). By referencing the predetermined or expected EBR line location information, the composite representation can be reviewed, "searching" for an EBR line feature at the expected location. The existence, or lack thereof, of an EBR line feature at the expected location is then established as the extracted feature attribute.

Alternatively or additionally, the feature attribute extracted at 208 can differ from those described above (e.g., feature intensity (or mathematical characterizations thereof such as mean intensity, standard deviation, etc.) as reflected in the composite representation, characterization of one or more pre-determined segments of a feature in the composite representation, an etch profile an EBR line feature, a frequency of an EBR line feature, an extent of parallelism of wafer edge top feature relative to an outer perimeter of the wafer, etc.). In other embodiments, two or more of the above described feature attributes (or other feature attributes) can be extracted at step 208. For example, the standard deviation, extent of completeness, and etch profile of every EBR line feature reflected in the composite image can be extracted as feature attributes. In this regard, the controller 158 can be programmed with one or more default feature attributes to be extracted. In addition or alternatively, the controller 158 can be programmed to extract feature attribute(s) selected or inputted by a user. For example, the controller 158 can be programmed to present a list of possible feature attributes to a user, with the user then selecting the feature attribute(s) of interest.

Regardless of type/format and number, the extracted feature attribute(s) are automatically assessed by the controller 158 (or other computing device) at step 210. The assessment(s) can take a variety of forms, and is generated as a function of the particular extracted feature attribute being assessed. For example, the extracted feature attribute can be compared to a value or range of values, such as a tolerance value or tolerance range (e.g., an extracted EBR line feature mean width attribute can be compared to a predetermined range; an extracted EBR line feature centricity percentage can be compared to a predetermined minimum value; etc.). Further, corresponding extracted attributes for two or more features can be compared to one another (e.g., line-perimeter offset standard deviation attribute of a first EBR line feature is compared to the line-perimeter standard deviation attribute of a second EBR line feature, etc.). The assessment can further entail a characterization or evaluation of the likelihood of one or more EBR line conditions indicative of defects or near-defects, such as jaggedness, scalloping, splashing, edge strength, EBR line overlap, etch profile, or other condition. Using the determined resist edges 114a, 114b a roughness measurement for the resist edges 114a, 114b, for example, or standard deviation number representative of how jagged or smooth the resist edges 114a, 114b is can be determined.

Additionally, it is contemplated that a basic shape of the resist edges 114a, 114b can be determined (e.g., circular, elliptical, etc.). Where multiple EBR lines are identified, such as resist edges 114a, 114b, "criss-cross" points, or intersections, of the EBR lines can be determined as well as offset between the multiple EBR lines. The above-listed metrics are not meant to be an exclusive list and other potential metrics are also contemplated.

In more general terms, then, the assessment at 210 can be any evaluation-type analysis performed on the extracted feature attribute that generates information indicative of one or more of a defect, near-defect, or fabrication processing deviation. In some embodiments, the generated information can alternatively or additionally be interpreted or viewed as indicating the lack or absence of a defect, near-defect, or fabrication processing deviation of interest (i.e., that the wafer being inspected likely did not have a particular defect or near-defect of interest, did not indicate a likelihood of a particular fabrication processing deviation, etc.). As a point of reference, a "defect" can be defined as being a condition that the manufacturer of the wafer 50 has deemed as requiring correction. Conventionally, semiconductor manufacturers (and/or their customers) establish standard criterion for certain semiconductor parameters or tolerances that in turn are applied to the wafer; any component outside of these tolerances will be rejected. Thus, a "defect" can be a condition having industry-wide applicability, or can be specifically generated by a particular manufacturer.

The criterion or other bases upon with the assessment is performed can assume a variety of forms. For example, the controller 158 can act upon user-inputted information relating to feature attribute, with the user information providing a quantification of an "acceptable" feature attribute (e.g., the manufacturer can designate a range within which a determined EBR mean line width must fall). Alternatively or additionally, the controller 158 can be programmed with default assessment parameters (e.g., the controller 158 can be programmed to assess a wafer exhibiting an absence of an expected EBR line as being defective). Even further, the controller 158 can be programmed to review a golden image or other information from which an assessment of the feature attribute can be based such as historical data.

In addition or as an alternative to an evaluation of whether the wafer is acceptable, the assessment at 210 can include correlating the extracted feature attribute(s) with yield information and/or fabrication processing step(s). More particularly, the assessment can include evaluating whether the extracted feature attribute is indicative of possible decrease in yield. That is to say, while the wafer may be deemed to have "passed" manufacturer-designated tolerance criterion at the intermediate fabrication stage at which the inspection was performed, the extracted feature attribute (either alone or in further view of other inspected wafers at a similar stage of fabrication) may indicate that in the absence of process modifications, the wafer following final fabrication will have a lower than desired component yield (e.g., edge die yield). This form of assessment can be performed, for example, by referencing historical data or information relating to the extracted feature attribute(s) from other wafers previously generated by the same fabrication processing in combination with their resultant yield values. In this regard, the controller 158 can be programmed (or linked to a separate processor or module) to determine a correlation between one or more feature attributes and component yield, for example by statistically or probabilistically comparing yield data and feature attribute data from previous wafers and relating this correlation to the extracted feature attribute of the wafer currently being inspected. But one, non-limiting example of this correlation is historical data suggesting that where a particular EBR line width has a standard deviation of greater than X and a concentricity of less than Y, component yield decreased by 3% compared with wafers not exhibiting theses same characteristics. Under these circumstances, then, where the extracted feature attributes of the current wafer being inspected include the particular EBR line width standard deviation being greater than X and a concentricity of less than Y, the assessment will determine that the wafer being inspected is likely to have decreased component yield at the end of fabrication. Other correlation factors or techniques are equally acceptable. Further, a plurality of different assessments can be performed.

Following the assessment, information is generated relating to a status of the fabrication processing at 212. The generated information can assume a variety of forms and is a function of the assessment. Further, step 212 can include determining corrective action(s), if any, responsive to the assessment, as well as conveying and/or automatically implementing the corrective action(s). For example, and with additional reference to the monitoring method 200' reflected in FIG. 6, the assessment 210 can indicate that there are no defects and no process deviations. Under these circumstances, the information relating to a status of the fabrication processing 212 (referenced generally in FIG. 6) includes a designation that the wafer is acceptable and optionally that no alterations to the fabrication processing steps are necessary, as reflected at 214. The monitoring method 200' than continues by processing a next wafer/substrate as shown.

Alternatively, where the assessment at 210 indicates that the wafer is defective, this condition is designated at 216. An evaluation is performed on the assessed defective condition at 218 to determine whether the defective condition is a random defect. If the defect is random ("yes" at 218), an evaluation of the defect is made to determine whether the wafer/substrate can be salvaged or repaired at 220. If the wafer/substrate can be repaired ("yes" at 220), the need for additional fabrication processing step(s), along with the existence, and optionally type, of the defect are conveyed (e.g., displayed on a display screen, printed in paper form, etc.) to a user at 222. In some embodiments, the generated information further includes the type and/or extent or remedial processing required or recommended is also conveyed to the user. Conversely, where it is determined that the wafer/substrate cannot be repaired and/or that the likely component yield will fall below a cost-effectively level ("no" at 220), an indication that the wafer/substrate should be scrapped is provided at 224.

If the defect is determined to be non-random ("no" at 218), an evaluation is performed at 226 to estimate whether the defect is due to a random fabrication processing variation. In this regard, the evaluation of the fabrication processing in view of the defect can be performed on a variety of bases. For example, the controller 158 can be programmed to automatically designate that certain defects are due to non-random process variations, while other are due to random process variations (e.g., a "missing" EBR line is a result of random process variation such as an operator error in operating a resist applicator, whereas a non-centric EBR line defect is a result of a non-random process variation such as a misaligned handling tool). Alternatively or additionally, the controller 158 can reference historical data and/or other extracted feature attributes to complete the evaluation. By reviewing the same feature attribute(s) of prior wafers, a processing drift can be recognized, for example, and deemed a non-random process variation (e.g., a progressively increasing EBR nominal line drift is indicative of an offset in handling equipment).

Regardless, if the process variation is determined to be random ("yes" at 226), the repairability of the wafer/substrate is evaluated at 220 and conveyed to a user as described above.

Conversely, if the process variation is determined to be non-random ("no" at 226), one or more fabrication processing step modifications are determined at 228 for correcting the process variation. The corrective processing modification(s) can be relative to processing steps before ("upstream") and/or after ("downstream") the current stage of fabrication of the wafer being inspected. For example, where the wafer is being assessed immediately following bevel cleaning (or edge bead removal), processing steps likely to implicated by the assessment include lithography application and/or edge bead removal (or other bevel cleaning techniques). Depending upon the particular assessment, then, one or more of these EBR line-related processing steps may be fine-tuned or otherwise modified. For example, the assessment may determine that handling equipment has become misaligned, that optical equipment is operating a less-than optimal time periods, etc. In this regard, the controller 158 can be programmed to automatically correlate a particular feature attribute assessment result with a particular process parameter modification and/or to reference user-entered process correlations. Alternatively, the controller 158 can reference historical data to determine a process step and/or equipment likely to be the cause of a particular process variation, and iteratively determine a desirable process modification (e.g., via artificial intelligence, probabilistic statistical analysis, etc.). By implementing the process modification(s), then, future wafers fabricated by the fabrication processing will be less likely to exhibit the same concerns evidenced by the current wafer being inspected (a desired goal that can be "confirmed" by the controller 158 in monitoring or inspecting future wafers).

In addition or as an alternative to modifying upstream fabrication processing steps and/or equipment, the process modification(s) determined at 228 can be downstream of the current fabrication stage. In connection with such downstream or remedial-type process modification(s) (e.g., modifying an existing fabrication processing step/equipment, adding an additional step to the fabrication processing, etc.), a timing of the process modification(s) can also be generated, such as by "smart schedule" in which an additional processing step is caused to occur at an optimal manufacturing stage and or time of day. Regardless, when implemented, the current wafer, as well as future wafers in some embodiments, will thus be more likely to exhibit enhanced component yield.

The so-generated process modification(s) can be effectuated in one or more fashions. In some embodiments, the process modification(s) are delivered to a user (e.g., displayed on a screen, printed instructions, etc.), with the user then assuming responsibility for reviewing and causing the suggested or recommended modification(s) to be implemented. In other embodiments, the controller 158 is programmed to automatically effectuate the determined fabrication modification(s). For example, the controller 158 can be electronically connected (e.g., directly connected or indirectly connected via a common server or other processor) with a separate controller that is otherwise operating to control a particular fabrication processing step/equipment. With this system construction, the controller 158 operates to automatically instruct or prompt the separate controller to automatically implement the determined process modification. Thus, the system 150 effectively provides a closed-loop control over fabrication processing.

Figure 6:
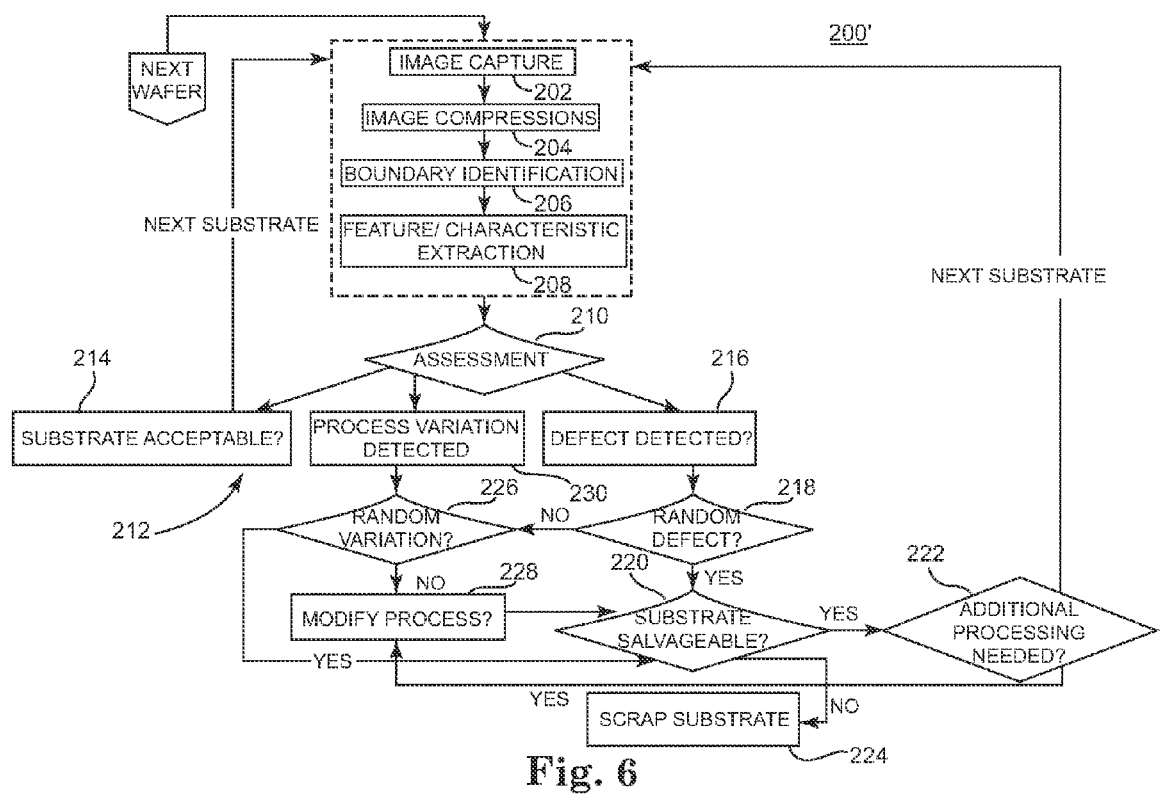
FIG. 6 is a flow diagram illustrate alternative methods of monitoring semiconductor fabrication processing in accordance with principles of the present disclosure.

FIG. 6 further reflects that the assessment 210 can indicate that while the wafer is not defective, the extracted feature attribute(s) are indicative of a possible process deviation.

Under these circumstances, the generated fabrication processing status information at 212 can include reviewing the detected process variation at 230. In connection with this review, a determination of whether the implicated process variation is a random variation is made at 226, with the method 200' proceeding as previously described. Once again, as a result of these evaluations, nominal (upstream) process parameters can be adjusted (either via instructions given to a user or automatically by the controller 158) to better ensure that subsequently fabricated wafers are less likely to suffer component yield losses, and/or remedial (downstream) process parameters can be adjusted or implemented (for example, automatically adjusted or implemented to better optimize the current wafer, as well as possibly future wafers.

In more general terms, then, the systems and methods of the present disclosure facilitate fine-tuning of fabrication processing. Actual or potential processing deviations are recognized and quickly addressed. Further, component yield (e.g., edge die yield) can be dramatically improved, on a relatively real-time basis. In this regard, the systems and methods of the present disclosure can act upon not only pass/fail defect detection, but also upon circumstances deemed to be indicative of a process deviation. For example, conditions indicative of less than optimal film adhesion can be viewed as being a possible, correctible deviation; off-set EBR lines can be viewed as being a possible, correctible deviation (e.g., tools generating the EBR lines are off-set); etch profile inconsistencies can be viewed as being indicative of possible, correctible deviations (e.g., poor adhesion); etc. As a result, the systems and methods of the present disclosure facilitate optimal control over a number fabrication processing tools. For example, in the specific context of EBR line inspection, tools such as a spin coater, edge polisher, wet and dry bevel etchers, optical etchers, etc., can be controlled. As a point of reference, any bevel cleaning operation/equipment can be controlled, with the term "bevel cleaning" being inclusive of EBR. Further, tooling/equipment relating to resist application can also be controlled, including dry-type lithography equipment and immersion-type lithography equipment. A variety of different upstream and/or downstream processing steps (relative to the processing stage of the wafer being inspected) can be correlated with extracted feature attributes and, for example, yield data to automatically identify, and correct, possible processing deviations. Any feature attribute giving rise to information indicative of a possible fabrication processing modification can be considered and acted upon.

Image Compression

Figure 7A:
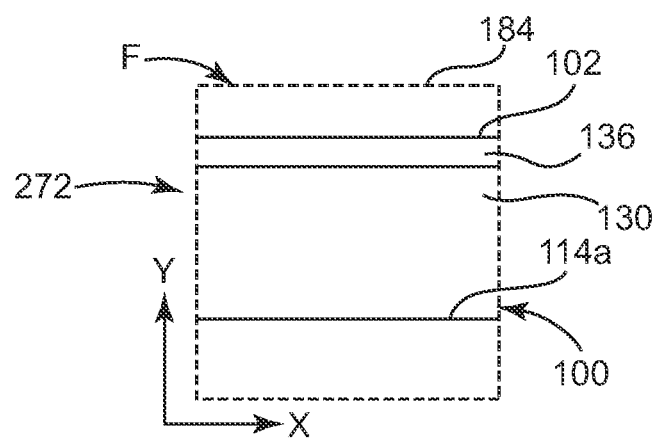
FIG. 7A is a schematic view of an image of a top edge region acquired during an inspection portion of methods in accordance with principles of the present disclosure.
Figure 7B:
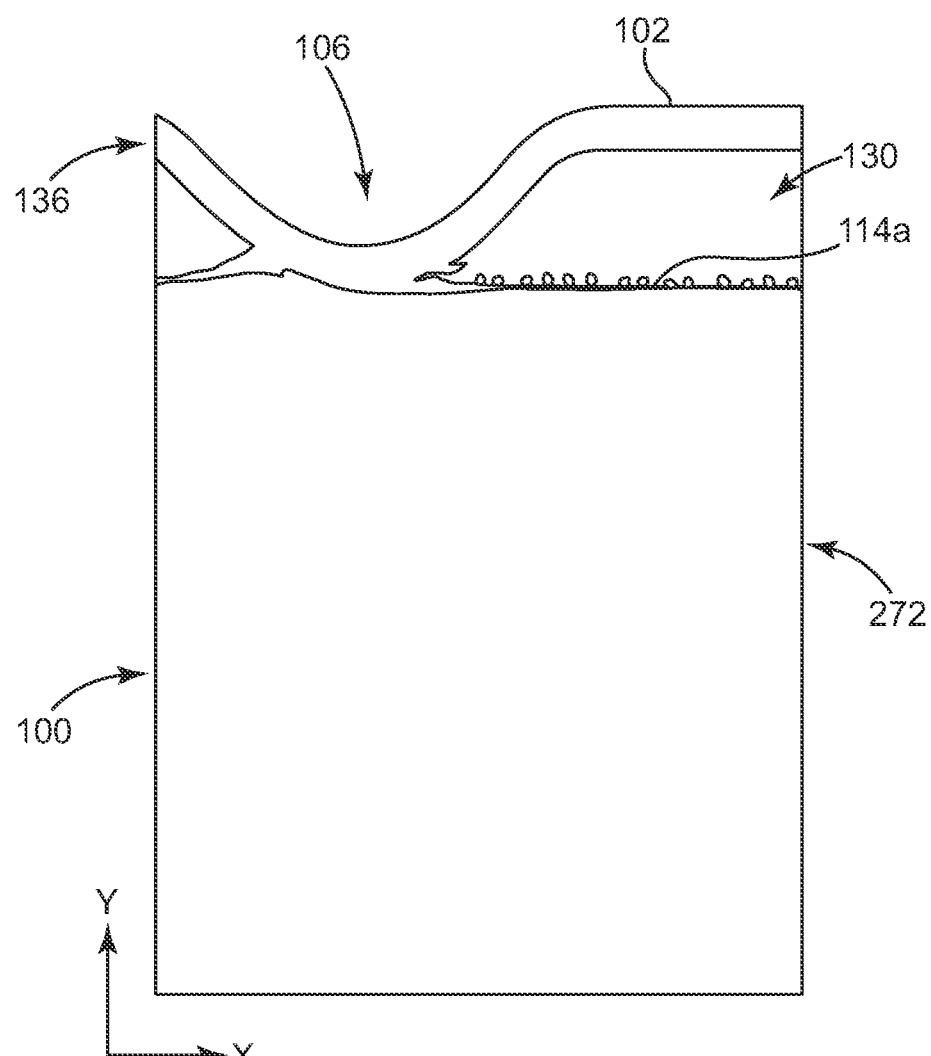
FIG. 7B is an example of an image of a top edge region showing a wafer notch.

As indicated above, image compression (204) serves to facilitate rapid performance of the methods of the present disclosure. Image compression can be performed using a variety of techniques, acceptable examples of which are described in U.S. Pat. No. 7,197,178 and in U.S. patent application Ser. No. 11/525,530 filed Sep. 22, 2006 and entitled "Wafer Edge Inspection and Metrology" the teachings of both of which are incorporated herein by reference. In general terms, one form of image compression references multiple, adjacent images of the wafer 50. FIG. 7A is a generalized, schematic representation of a first image of the plurality of images taken at a first frame acquisition location F during image data acquisition (e.g., image capturing at 202) according to some embodiments. For additional reference, FIG. 7B is one example of an image of the top edge region 100 acquired according to related embodiments of the present invention, FIG. 7B also showing the notch 106. Returning to FIG. 7A, each of the plurality of images comprises a pixel array, with the first image comprising a first pixel array 272. The pixel array 272 is described in more detail to illustrate principles that are applicable to each of the plurality of pixel arrays associated with the plurality of images. In general terms, the pixel array 272 comprises a plurality of pixels arranged in an array, with the pixel array 272 having a first dimension X and a second dimension Y. Each pixel of the pixel array 272 has an associated pixel characteristic value, such as a brightness value, with wafer features, such as the first resist edge 114a, the exposed edge region 130, the first resist edge 114a, the top bevel 136 the bottom edge region 134, and wafer edge normal 138 causing variations in the pixel characteristic values.

Pixel characteristics optionally include grayscale brightness information, although other types of information, color data, for example, are also contemplated. For example, some embodiments include using a filter or other means to acquire red, blue, and/or green light intensity image data. Additionally or alternatively, combinations of grayscale and color data, such as red, blue, and/or green data is optionally acquired and analyzed, for example using a Bayer camera. Additionally, it is contemplated that a pixel characteristic value optionally corresponds to a height value of the pixel in some embodiments. From the above, it should be understood that a variety of types pixel characteristic values are contemplated, including those associated with any pixel characteristics that are representative of one or more wafer features.

In some embodiments, the first dimension X of the pixel array 272 is substantially tangential to wafer 50, and in particular wafer edge 102, with the dimension Y being substantially radially aligned to the wafer 50, although other orientations of the pixel array 272 are also contemplated, or may result due to wafer offset during inspection, for example. In one embodiment, the pixel array 272 comprises an array of 1,600 horizontal pixels across the first dimension X by 1,200 vertical pixels across the second dimension Y (1,920,000 pixels), although other pixel arrays are contemplated. For example the pixel array 272 is optionally 1,920 pixels across the first dimension X by 1,078 pixels across the second dimension Y (2,069,760 pixels).

Image data compression 204 (FIG. 5) includes compressing the acquired images. In particular, the plurality of pixel arrays are each compressed in the first dimension X, resulting in a plurality of compressed pixel arrays. In some embodiments, compression of the pixel arrays results in the compressed pixel arrays being spaced apart from one another at their respective image frame locations about the wafer 50. In other words, unless there is an extreme amount of overlap between the acquired images and/or a relatively low amount of compression, there will be some "spacing" between the compressed pixel arrays according to their respective image frame locations. In some embodiments, image compression assists in removing or reducing image information relating to wafer patterning, random variations in image data, or other undesirable image information. Such patterns or other random variations can otherwise cause difficulties in finding the first resist edge 114a, as well as other wafer features.

In some embodiments, compression is achieved in first dimension X alone, with the second dimension Y remaining entirely "uncompressed" or "non-compressed." Regardless, compression, for example across the first dimension X, is accomplished via a variety of methods. For example, the pixel characteristic values of the pixel arrays are optionally averaged across the first dimension to get an average pixel characteristic value. In some embodiments, pixel array 272 is compressed by averaging the brightness values of the pixel array 272 across the first dimension X to generate a single column of pixel brightness values in the second dimension Y.

In somewhat different terms, the plurality of acquired images are optionally compressed by averaging pixel rows, across the first dimension X, resulting in a multitude of images that are full depth in the second dimension Y, but only one pixel wide in the first dimension X. It is also contemplated that the pixel characteristic values of the pixel array 272 are optionally compressed to more than a single column of pixels or otherwise as desired.

Utilizing compression, pixel characteristic variations that are not of interest (such as random image variations or wafer patterning) across the first dimension X can be reduced to highlight variations from desired features, such as more regular features that extend along the first dimension X. Thus, image compression along the first dimension X can be used to perform noise and/or undesirable edge suppression, for example. In more conceptual terms, in some embodiments, image variations or aberrations that do not extend along the first dimension X are substantially reduced to bring out or otherwise highlight wafer features that more or less extend circumferentially about the wafer top edge region 100, although features extending in other directions/having other shapes can also be highlighted as desired. Thus, brightness variations, for example, in the pixel array 272 due to such features as the wafer edge 102 (FIG. 2), the first resist edge 114a (FIG. 2), the top bevel 136 (FIG. 3), a silicon or insulator layer edge (not shown), or the exposed edge region 130 (FIG. 3), can become more pronounced, or retain their relative strength(s). In turn, more random brightness variations, or features that do not substantially extend circumferentially about the wafer 50, such as die patterns (not shown) or test patterns (not shown) on the wafer 50, are filtered or become less pronounced. This can be particularly advantageous where wafer patterning crosses or otherwise interferes with an EBR line or other wafer feature to be located.

It should also be understood that image compression is optionally performed additionally or alternatively in another direction, not tangential to the wafer edge 102, in order to highlight and/or filter out a variety of other image artifacts or variations as described. Furthermore, similar image compression principles are applicable to images acquired of the wafer edge normal 138 and/or bottom edge region 134, for example. In some embodiments, where regular features on the wafer 50, e.g. streets, missing die, notches, flats or fiducials, undesirably show up in a compressed image, such features often will most likely have a recognizable signature. While these signatures may vary in terms of appearance, it is contemplated that they will tend to appear in a compressed image in predetermined locations related to their actual locations on the wafer 50. Accordingly, these signatures may be removed, either automatically or manually. In some embodiments, automatic removal of these signatures may involve the use of image recognition algorithms or techniques to identify and remove such signatures. Manual and/or automatic removal may involve, in some embodiments, selecting a regular feature to be removed from analysis, such as by defining a region of interest that surrounds the regular wafer feature and instructing the controller 158 to ignore image data from that region, and removing image data prior to image compression and/or following image compression as desired.

Although compressed images are optionally analyzed to locate or otherwise characterize various wafer features, in some embodiments, the wafer edge 102, the top edge bevel 136, and/or the first resist edge 114a are located using a best-circle-fit to the plurality of spaced-out, compressed pixel arrays. A location of the wafer center 104 and/or the resist center 112 can then be determined. In other words, one or more wafer features are optionally determined from "un-concatenated" or "non-concatenated" data according to image frame acquisition location. However, as described below, analysis of concatenated, composite image data is used in some embodiments in order to locate/identify one or more wafer features, as well as features associated with the bottom edge region 134 as desired.

Image data concatenation can also be performed, prior to or following image compression. However, concatenation of the compressed pixel arrays can be more efficient in some embodiments, as less data is operated upon in order to perform the concatenation (millions of pixels for each image being concatenated in comparison to thousands of pixels, for example).

Figure 8:
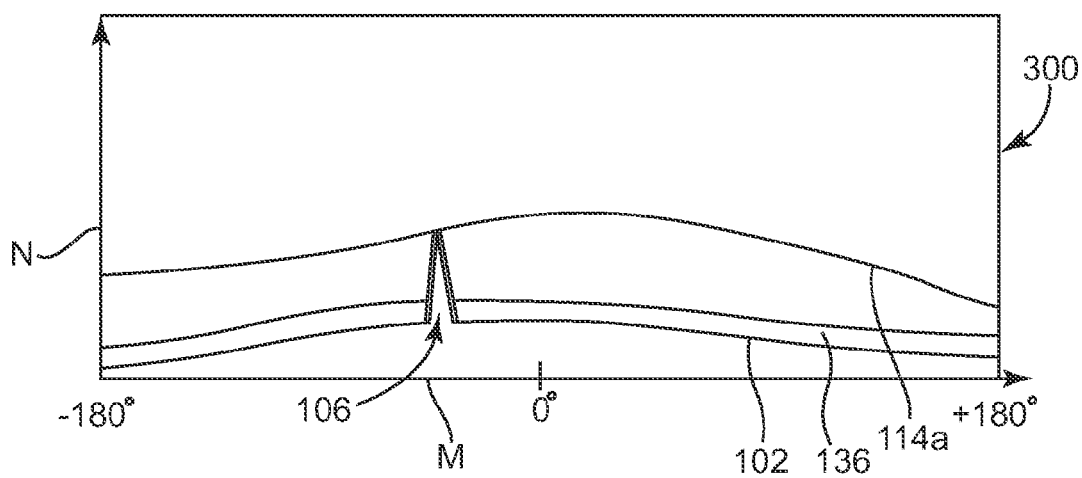
FIG. 8 is a schematic view of a composite representation of compressed images in accordance with principles of the present disclosure.

FIG. 8 is a generalized, schematic illustration of the compressed pixel arrays acquired of the top edge region 100 (see also FIGS. 2-4) concatenated into a composite representation 300 having an associated first axis M and a second axis N in accordance with some embodiments. For reference, the terms "stitching" and "concatenating" are used interchangeably herein and generally refer to either aligning overlapping image data as well as aligning image data in an "edge-to-edge" fashion, as appropriate. As described in greater detail below, the composite image 300 is analyzed to locate or otherwise characterize one or more wafer features, such as the first resist edge 114a, the wafer edge 102, the top bevel 136, the wafer center 104 (FIG. 2), the resist center 112 (FIG. 2), or any other wafer features including others expressly or implicitly described herein.

In general terms, each of the plurality of compressed pixel arrays are aligned to one another in a sequential manner (e.g., according to an angular position of the image frame acquisition location at which they are taken about the wafer 50). Concatenation is performed using a concatenation algorithm, such as concatenation algorithms known to those of ordinary skill in the art. The concatenation algorithm or other concatenating program module is applied to the plurality of compressed pixel arrays in order to help ensure that the images are properly aligned. Thus, in some embodiments where the plurality of compressed pixel arrays have been compressed into a single column of pixels, the composite image 300 comprises each of the columns of pixels aligned as desired in a sequential manner according to the angular position of their respective image frame acquisition locations about the wafer 50.

As referenced above, the composite image 300 is "filtered" via the pixel array compression previously described such that wafer features which extend in a substantially circumferential manner about the wafer 50 are more readily identified via edge detection and region growing techniques, for example, as described in greater detail below. In some embodiments, the first and second axes M, N generally correspond to the first and second dimensions X, Y, respectively, of each of the compressed pixel arrays. The first axis M is described in angular units, such as 0 degrees to 360 degrees or −180 degrees to +180 degrees, for example, while the second axis N is described in units of distance, micrometers, for example.

With reference between FIGS. 2 and 8, where the wafer 50 is well-centered during imaging of the top edge region 100, for example, and in the absence of other imaging deviations, the wafer edge 102 should be represented in the composite image 300 as a substantially straight line. However, where alignment errors occur, for example, where the wafer 50 is offset to some extent on the stage assembly 162, the wafer edge 102 will take a more sinusoidal shape in the composite image 300 as indicated generally in FIG. 8. In other words, the offset of some embodiments induces eccentricity in the imaging of the wafer edge 102, which results in the wafer edge 102 taking a more sinusoidal shape due to the fact that the wafer edge 102 according to the circularity of the wafer edge 102.

In a similar manner, the first resist edge 114a is also shown in FIG. 8 to have a somewhat irregular, non-linear shape. Where the first resist edge 114a is at a substantially regular distance from the wafer edge 102, for example where the wafer center 104 and the resist center 112 are aligned well, the first resist edge 114a will track the wafer edge 102, the two having a substantially similar shape. In turn, where the first resist edge 114a varies in distance relative to the wafer edge 102, the shape of the wafer edge 102 and the resist edge 114a become more disparate, for example where the layer of resist 108 is not centered on the wafer 50. Thus, where the wafer center 104 is centered with the resist center 112, and the wafer 50 is centered on the stage assembly 162 (and in the absence of other imaging eccentricities, for example), both the wafer edge 102 and the first resist edge 114a will extend in a substantially linear manner within the composite image 300. Where the distance between the first resist edge 114a and the wafer edge 102 is substantially constant about the entire circumference of the wafer 50, but where the wafer 50 is not centered during imaging, for example, the wafer edge 102 and the first resist edge 114a will have more sinusoidal shapes, each of the sinusoids tracking well with one another. However, as variability between the first resist edge 114a and wafer edge 102 increases, the sinusoidal shapes of the wafer edge 102 and the shape of the first resist edge 114a will generally become more and more disparate.

Figure 9A:
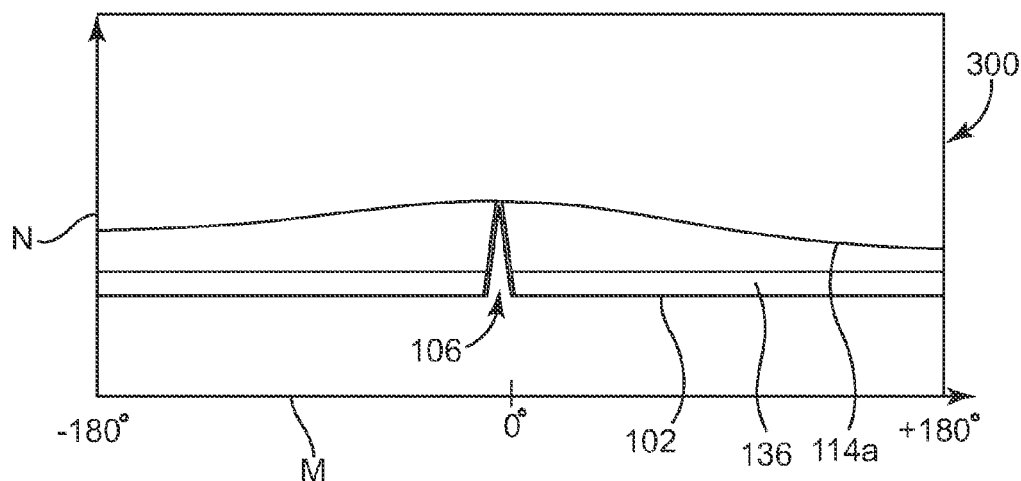
FIG. 9A is schematic a view of the composite image of FIG. 8 following normalization to a found wafer edge.
Figure 9B:
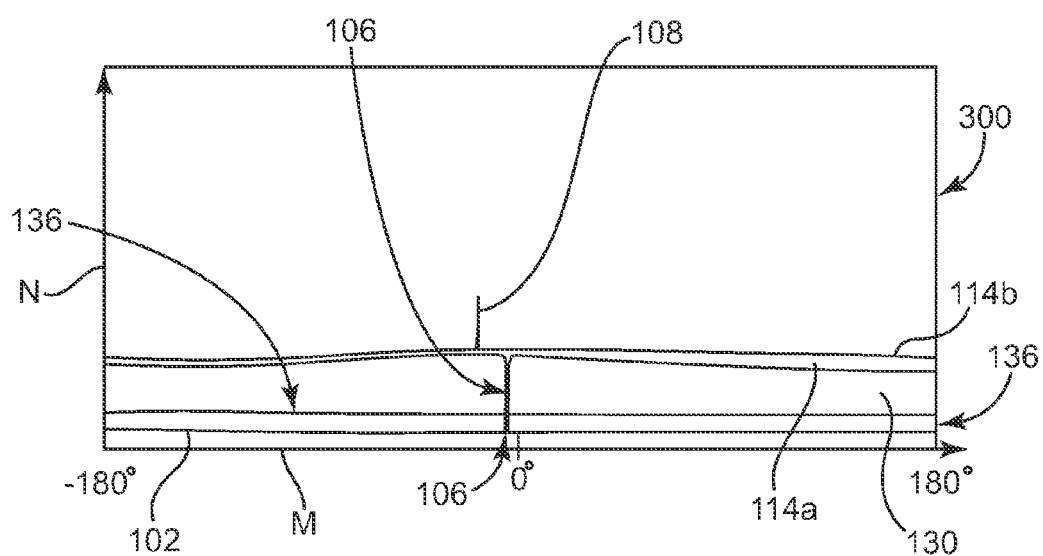
FIG. 9B is an example of a normalized composite image generated during an edge inspection portion of methods in accordance with principles of the present disclosure.

With reference to the generalized, schematic view of FIG. 9A, in some embodiments, the composite image 300 of the top edge region 100, for example, is normalized to the wafer edge 102. FIG. 9B shows an example of the composite representation 300 acquired according to some embodiments and normalized such that the wafer edge 102 is substantially straight. Of note, FIG. 9A shows the first resist edge 114a highlighted, while embodiments of the first and the second resist edges 114a, 114b are visible in FIG. 9B. Regardless, the wafer edge 102 is optionally located by applying one or more edge detectors to the non-concatenated compressed pixel arrays and applying a best-circle-fit. In other embodiments, the wafer edge 102 is located in the composite image 300 in a similar manner to the first resist edge 114a, as described in greater detail below. Regardless, the composite image 300 is optionally normalized based on the found wafer edge 102, such that the composite image is shifted with the found wafer edge 102 being a straight line, although the composite image 300 can be normalized such that the wafer edge 102 takes on other shapes as desired.

Figure 10:
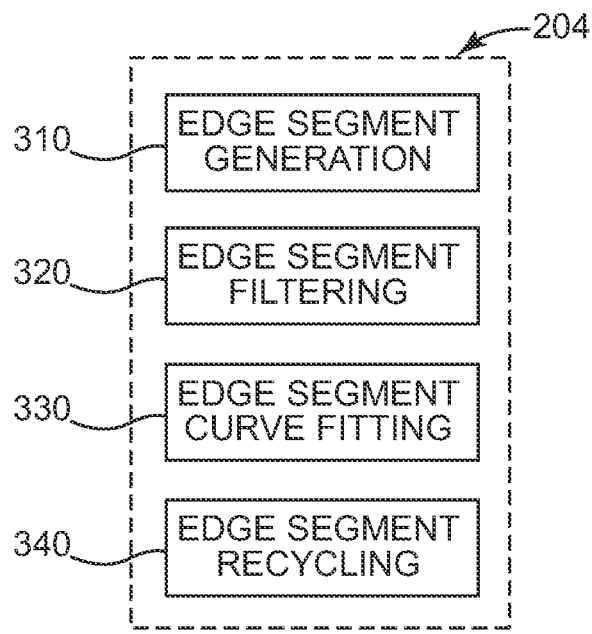
FIG. 10 is a flow diagram of a portion of another monitoring method.

With reference to FIG. 10, composite representation generation and/or analysis can further include Edge Segment Generation 310, Edge Segment Filtering 320, Edge Segment Curve Fitting 330, and Edge Segment Recycling 340. Edge Segment Generation 310 includes applying one or more edge detectors to the composite image 300. In some embodiments, a Sobel edge detector and a Canny edge detector algorithm are applied to the composite image 300 to generate edge gradient data corresponding to the pixels making up the composite image 300. Upper and lower gradient thresholds, as well as other criteria, are set as desired either automatically or manually in order generate edge segment data or otherwise grow one or more edge segments corresponding to a feature to be located or otherwise characterized from the edge gradient data. For example, based on a starting pixel characteristic and edge threshold condition (contrast in some instances), edge segments are "grown" by adding pixels to a segment grouping if they meet the selected edge segment threshold conditions.

In some embodiments, Edge Segment Filtering 320 includes using edge segment intensity cross-section is analyzed to determine a profile of an edge segment, which can be indicative of a resist edge, such as the first resist edge 114a, and/or noise and allows bad edge segments to be discarded or prefiltered before or during curve fitting. If desired, a user is allowed to adjust upper and lower edge gradient thresholds, edge strength threshold (e.g., average edge segment edge gradient), and/or segment size thresholds (for example a minimum edge segment length) to disregard or highlight particular edge segments in order to facilitate wafer feature identification. It is also contemplated that the edge inspection system 150 automatically adjusts or selects such criteria in some embodiments. In this manner, edge segments are filtered to a particular size, edge strength, and/or minimum gradient value, or according to other criteria, prior to, Edge Segment Curve Fitting 330, although such filtering may alternatively or additionally occur during or after Edge Segment Curve Fitting 330.

Edge Segment Curve Fitting 330 includes identifying edge segments of a plurality of generated edge segments that correspond to a selected wafer feature. In some embodiments, Edge Segment Curve Fitting 330 includes selecting a first edge segment generated from the edge gradient and fitting a sinusoidal curve to the first edge segment. In particular, wafer features extending about the wafer 50, such as the first resist edge 114a, silicon or insulator layer edges (not shown), the bevels 136, 140, the wafer edge 102, and others are represented well by sinusoidal lines. This is at least partially attributable to the circular, including annular, shape of such wafer features. In particular, this result is understood with reference to the generally understood relationship between circles and sinusoids and that an eccentrically positioned EBR line will generally appear as a sinusoid in the composite image 300. Thus, based on an assumption that the first resist edge 114a is substantially circular, eccentricity between the wafer 50 and the layer of resist 108 results in a sinusoidal shape in the composite representation 300. As such, sinusoidal curve fitting, for example using Least Squares optimization techniques, is applied to fit a first curve to the detected segments. However, other types of curves or line fitting are also contemplated for curve fitting the edge segments. For reference, it should be understood where the wafer feature to be located using sinusoidal curve fitting is substantially straight, a sinusoid having a small or substantially no amplitude will be fit to the feature to be located.

In some embodiments, one or more subsequent edge segments are identified and segment distance (average, median or and/or absolute) from the first sinusoidal curve fit is calculated to see if subsequent segments are a good fit with the first fit curve. Where a subsequent segment is a good fit, that segment is grouped, merged, concatenated, or the like, with a first group of segments and a subsequent, second sinusoidal curve is fit to the new first group of edge segments. In some embodiments, this process continues iteratively until a potential feature, such as the first resist edge 114a, is characterized to a desired extent, for example as measured by a desired number of edge segments. In one embodiment, a potential wafer feature, such as a potential EBR line, is disregarded if edge segments corresponding to a fit curve are only identified across some total percent of the composite image 300. For example, a lower bound could be set that the edge segments associated with a particular fit curve must cumulatively extend across 60%, 80%, or upward to 100% of the composite image. Thus, in some embodiments, an iterative curve fitting process for a particular group of edge segments will continue until the group of concatenated edge segments identified by curve fitting extends across the entire composite representation 300.

Additionally, where edge segments have been disregarded from a particular curve fitting operation, for example as being too far from a curve being fit during an iterative process (as determined by another user input or predetermined threshold level, for example), a new curve fitting iteration can begin for fitting a new potential wafer feature line to such disregarded segments. Regardless, several potential wafer feature line candidates optionally result. In some embodiments, the wafer features are resist edges or EBR lines that are chosen from potential EBR line candidates according to their total length, cumulative edge strength, or other factors.

Edge Segment Recycling 340 includes reevaluating edge segments after an initial curve fitting process has been completed. For example, in some embodiments, edge segments which may or may not have previously been incorporated into one of the generated potential wafer feature lines or other edge segment grouping are reprocessed in an effort to further strengthen potential wafer feature identification edge segment candidates. In some embodiments, non-fitted, borderline, and/or fitted edge segments are reviewed and incorporated into one or more edge segment groups according to subsequent curve fitting analysis, such as by reevaluating edge segments according to more forgiving length or edge strength requirements in view of a relatively higher degree of proximity to a particular curve fit, for example.

Figure 11:
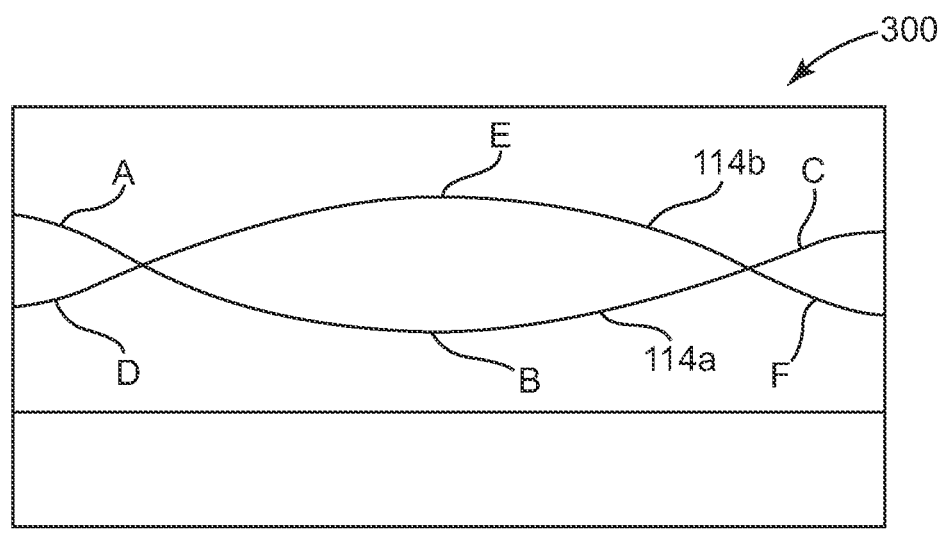
FIG. 11 is a schematic view of a composite representation generated as part of some methods in accordance with principles of the present invention.

With reference to FIG. 11, in some embodiments the above-described methodology is suited for finding multiple, crossing film edge lines, such as EBR lines belonging to separate, distinct resist layers. In particular, FIG. 11 illustrates some embodiments where the resist edge 114a has been found according to groupings of edge segments A, B, C and the resist edge 114b found according to groupings of edge segments D, E, F. With reference to FIG. 11, it should be understood that the sinusoidal curve fitting technique helps ensure that each of the groupings of edge segments A, B, C and the groupings of edge segments D, E, F are associated with each other to identify the resist edges 114a, 114b. In particular, edge segments A, B, C form a highly sinusoidal fit as do edge segments D, E, F, whereas other combinations of the edge segments A, B, C, D, E, F exhibit a lesser degree of sinusoidal fit for evaluating the resist edges 114a, 114b.

It will be understood that the above-described examples of image compression are but a few acceptable techniques in accordance with the present disclosure, and that other approaches can also be employed. For example, a variable image compression process can be utilized. As a point of reference, compression speeds the inspection/analysis process. Because, for example, on the wafer top side compression is needed to minimize or remove any superfluous patterns, compression should be optimized with respect to the amount of pattern present. Edge normal EBR line metrology requires less compression because there is no repetitive patterning on the edge, and more or less regular features of the EBR line(s) can be "picked out" of the random features on the edge normal. Optimization of the compression in the edge normal images can be based on a balancing of processing speed (e.g., throughput) and resolution. The higher an image is compressed, the faster the processing speed. But, at higher compressions, it can be more difficult to resolve or "fit" an estimated EBR line to the captured image(s). As such, optimization can be achieved based upon a user's intuition concerning past results or based on knowledge of the EBR characteristics. This "user defined" inspection criteria can be defined as a compression level that is within predetermined limits set or selected by a user. Alternatively, optimization can be accomplished via a statistical approach, such as by computer-based line fitting in which an objective scoring bases (summing, averaging, or other analysis of pixel location difference) can be used to determine whether a fit is "good." If the fit is not good, a lower compression rate can be employed, and the resultant score checked for acceptability. Even further, the relative positions of pixels in the compressed image (or other representation) can be reviewed to determine whether they are too far apart. If adjacent pixels in the compressed image are far apart from one another, this condition is indicative that the EBR line feature in question is highly variable (e.g., jagged) and/or that more than one EBR line feature, with one of the EBR lines having a fainter signature.

In some embodiments of image compression, the level of compression is selected so as to maximize the resolution of the resulting images. In one embodiment, where the feature or object of interest, e.g. an EBR line, includes relatively high frequency variation, very high levels of compression will be less desirable or necessary resolution of the high frequency variation will be lost. This optimization process may take place regardless of where the feature or object of interest is located, i.e. optimization may be employed for edge top, bevel top, edge normal, bottom bevel, and edge bottom images and/or inspection processes. Accordingly, where a high frequency variation in an EBR line visible in an edge normal image is being analyzed, compression of the acquired images may be two to three times lower than for an edge top acquired image in which a relatively low frequency feature or object is being analyzed. In real terms, this may mean that the aforementioned edge normal images may be compressed in the X direction to 2-3 distinct pixel columns instead of one single pixel columns. The period or spacing of multiple compressed pixel columns is likely to regular around the periphery of the wafer, but may be asymmetrical around selected features such as a notch or the like.

EXAMPLES AND COMPARATIVE EXAMPLES

Testing was performed to verify that the systems and method of the present disclosure can provide rapid monitoring and related fine-tuning of semiconductor fabrication processing, and in particular the EBR process. In particular, in-process semiconductor wafers were inspected and monitored using conventional techniques as well as using an automated wafer inspection system incorporating backside and edge inspection as described above at several inspection steps. The edge inspection system scans the wafer edge, acquires a set of images and uses algorithms to detect a wide range of process-related or mechanically induced edge defects.

In addition to performing edge top and edge bevel inspection, the automated edge inspection system is able to perform automatic high-resolution Edge Bead Removal (EBR) metrology on both unpatterned and patterned wafers by using an algorithm on bright field images acquired by the edge top camera. As described above, during edge top inspection, the edge top sensor collects 360° of adjacent and/or overlapping images. The system stitches these images together and compresses them to form an "EBR fingerprint" map. From the EBR fingerprint, the locations of the wafer edge and EBR edge are calculated, along with their relationship to the wafer center. This compression improves the resolution of features located in the expected locations of EBR features and minimizes (almost to the point of removing) non-EBR features such as patterning on the wafer that may extend up to the edge of the wafer. Circular EBR features appear as vertical lines in the "EBR Fingerprint" map while oblong or off-centered EBR features appear as sinusoidal lines.

The automated edge inspection system provided a more comprehensive EBR metrology data set than the manual measurements taken on a conventional profiler. From this inspection, the automated edge inspection system calculated the EBR width around the perimeter of the wafer using up to 360 points; the standard deviation, which gives some indication of EBR line roughness; and the X and Y center and radial offset of the EBR relative to the wafer center.

EBR metrology data was collected on a set of 14 monitor wafers, which included wafers coated on two different coat tracks, using three different resists, both chemical EBR and optical EBR, and nominal EBR widths of 2.0 mm and 1.5 mm. The outer and inner EBR tolerances are +/−0.5 mm. All wafers were measured twice on a conventional profiler and five times on the automated edge inspection system to compare mean EBR width, within-wafer sigma, and measurement repeatability.

During this testing, the same profiler was used to collect all manual measurements. Two coat tracks which had historically exhibited the most variation in EBR were selected for testing. Wafer pairs were prepared having identical resist coatings and identical EBR techniques (either chemical EBR or optical EBR). Automated EBR measurements were taken once per day on all 14 wafers on the automated edge inspection system over a period of five days, collecting 360 data points around the perimeter of the wafer. EBR measurements were also measured twice for each wafer using the conventional profiler, collecting 3 data points, 120 degrees apart, on each wafer.

A comparison of the EBR measurements from the automated edge inspection system and the conventional profiler revealed a high degree of correlation, evidencing that the automated edge inspection system generated reliable results. The examples and comparative examples surprisingly illustrated that automated imaging (via, for example, the automated edge inspection system) affords the ability to monitor and control the EBR process on each coat track more than twice per week, while conventional profiler could be used simply as a backup tool. This will allow more frequent and consistent monitoring of the EBR process, and any excursions can be discovered before any product wafers are further processed. The run-to-run repeatability and within-wafer sigma values of the automated edge inspection system and profiler measurements are highly comparable. The experimental data further revealed that a correlation can be established between standard deviation and line quality, jaggedness, unevenness, and centricity.

The automated edge inspection system's EBR inspection and EBR metrology provide a more comprehensive data set that can be used to control the EBR process. In addition to calculating the EBR width around the entire perimeter of the wafer, this data includes the X and Y offset values and radial offset of the EBR region, which provide information about the centricity of the EBR placement. The comprehensive nature of the E20's data collection provides the ability to track EBR variations over the entire wafer. These variations are almost completely missed by conventional techniques of looking at only 3 points on the wafer.

The time required to measure 2 wafers using the conventional profiler is generally between 5 and 10 minutes. Using the automated edge inspection system tool can require only about 1 minute per wafer, which greatly enhances the efficiency of monitoring the EBR process with a much higher UPH in throughput.

The fabrication monitoring systems and methods of the present disclosure provide marked improvements over previous designs. By rapidly capturing and assessing extracted feature attribute(s), defects, such as EBR-related defects, are quickly recognized, and adjustments (if necessary) made. Further, process deviations, including less apparent process deviations that have a correlation to reduced component yield (e.g., resist application and/or EBR processes), can be recognized and addressed on a virtually real-time basis.

Although specific embodiments of the present invention have been illustrated and described herein, it will be appreciated by those of ordinary skill in the art that any arrangement that is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A method of monitoring semiconductor fabrication processing, the method comprising:
   capturing at least one image relating to an edge of a semiconductor wafer being prepared by the fabrication processing;
   compressing the at least one captured image to generate a composite representation of an edge zone of the wafer;
   identifying an edge bead removal area in the representation;
   extracting at least one feature attribute from the identified edge bead removal area, comprising:
      identifying an edge bead removal line represented in the identified edge bead removal area; and
      determining a value of a feature characteristic at a plurality of points along the edge bead removal line;
   automatically assessing the extracted feature attribute based on the value of the feature characteristic at each of the plurality of points; and
   generating information relating to a status of the fabrication processing based upon the assessment.

2. The method of claim 1, wherein capturing at least one image includes capturing a plurality of images, the plurality of images combining to represent an entirety of an outer circular perimeter of the wafer, and further wherein compressing the at least one captured image includes compressing the plurality of captured images to generate a singular representation of the edge of the wafer.

3. The method of claim 1, wherein compressing the at least one image includes:
   identifying information in the at least one image indicative of a possible edge bead removal line; and
   fitting the identified information to a straight line.

4. The method of claim 1, wherein compressing the at least one image includes:
   identifying information in the at least one image indicative of a possible edge bead removal line; and
   fitting the identified information to a curvilinear line.

5. The method of claim 1, further comprising:
   correcting the at least one captured image for tilt prior to the step of compressing.

6. The method of claim 1, wherein extracting at least one feature attribute includes:
   identifying a plurality of edge bead removal lines represented in the identified edge bead removal area; and
   determining a standard deviation of a common characteristic in each of the identified edge bead removal lines.

7. The method of claim 1, wherein extracting at least one feature attribute includes:
identifying an edge bead removal line represented in the identified edge bead removal area; and
determining an extent of completeness of the identified edge bead removal line.

8. The method of claim 1, wherein extracting at least one feature attribute includes:
reviewing information indicative of an expected edge bead removal line location relative to an outer periphery of the wafer; and
determining whether a representation of an edge bead removal line exists in the identified edge bead removal area at the expected location.

9. The method of claim 1, wherein extracting at least one feature attribute includes:
identifying an edge bead removal line represented in the identified edge bead removal area; and
determining a frequency of the identified edge bead removal line.

10. The method of claim 1, wherein automatically assessing the extracted feature attribute includes:
comparing the extracted feature attribute of a first identified edge bead removal line with a corresponding extracted feature attribute of a second identified edge bead removal line.

11. The method of claim 10, wherein the extracted feature attribute of the first and second identified edge bead removal lines is a standard deviation in line width, and further wherein the step of automatically assessing further includes evaluating likelihood of overlap between the first and second edge bead removal lines based upon the comparison.

12. The method of claim 1, wherein the extracted feature attribute relates to an etch profile attribute of an edge bead removal line feature on the wafer, and further wherein automatically assessing the extracted feature attribute includes:
comparing the etch profile attribute with pre-determined acceptable etch profile characteristics.

13. The method of claim 1, wherein automatically assessing the extracted feature attribute includes:
reviewing user inputted information relating to a quantification of an acceptable feature attribute.

14. The method of claim 1, wherein automatically assessing the extracted feature attribute includes:
reviewing historical data relating to the extracted feature attribute from other wafers previously generated by the fabrication processing.

15. The method of claim 1, wherein generating information relating to a status of the fabrication processing includes:
determining that the wafer is not acceptable;
determining whether subsequent remedial processing will render the wafer acceptable; and
designating the subsequent remedial processing as necessary for the wafer in addition to other process steps associated with the fabrication processing.

16. The method of claim 1, wherein generating information relating to a status of the fabrication processing includes:
determining that the assessment is indicative of an unacceptable deviation in at least one fabrication processing step occurring prior to the step of capturing at least one image; and
designating an adjustment to the at least one fabrication processing step.

17. The method of claim 1, wherein generating information relating to a status of the fabrication processing includes:
determining that the assessment is indicative of a need for altering at least one fabrication processing step occurring after the step of capturing at least one image;
designating an alteration to the at least one processing step;
implementing the alteration; and
fabricating a plurality of semiconductor wafers through the fabricating processing including the altered processing step.

* * * * *